United States Patent [19]

Andersen

[11] Patent Number: 5,252,464

[45] Date of Patent: Oct. 12, 1993

[54] PROCESS FOR PRODUCING PENTAPEPTIDES AND INTERMEDIATES FOR USE IN THE SYNTHESIS

[75] Inventor: Anders J. Andersen, Kokkedal, Denmark

[73] Assignee: Carlsberg Biotechnology Ltd. A/S, Copenhagen, Denmark

[21] Appl. No.: 940,772

[22] Filed: Sep. 4, 1992

Related U.S. Application Data

[63] Continuation of Ser. No. 493,508, Mar. 14, 1990, abandoned.

[30] Foreign Application Priority Data

Mar. 14, 1989 [DK] Denmark .............................. 1224/89

[51] Int. Cl.$^5$ .......................... C12P 21/00; C07K 7/00
[52] U.S. Cl. ........................ 435/68.1; 930/DIG. 802; 530/330
[58] Field of Search ................ 930/802; 530/330; 435/68.1

[56] References Cited

U.S. PATENT DOCUMENTS

| | | | |
|---|---|---|---|
| 4,161,522 | 7/1979 | Hamburger | 530/330 |
| 4,171,299 | 10/1979 | Hamburger | 530/330 |
| 4,668,625 | 5/1987 | Cambiaghi et al. | 435/68.1 |
| 4,816,449 | 3/1989 | Hahn | 930/10 |
| 5,037,741 | 8/1991 | Iacobucci | 435/70.1 |

FOREIGN PATENT DOCUMENTS

| | | | |
|---|---|---|---|
| 236346 | 6/1986 | Fed. Rep. of Germany | 435/68.1 |
| 90/10704 | 9/1990 | PCT Int'l Appl. | 435/68.1 |

OTHER PUBLICATIONS

Hamburger, Science 189, p. 389 (1975).
Merrifield, J. Am. Chem. Soc. 85: p. 2149 (1963).

(List continued on next page.)

Primary Examiner—Douglas W. Robinson
Assistant Examiner—Jon P. Weber
Attorney, Agent, or Firm—Fish & Richardson

[57] ABSTRACT

Pentapeptides having the formula H-Asp-Ser-C-Pro-Arg-OH, where Asp, Ser, Pro and Arg may have L- or D-configuration, and C denotes Asp or Asn in L or D configuration, are synthesized by reacting in an aqueous medium $Y_2$-Pro-OH, wherein $Y_2$ is a protective group, with Arg-Ro, wherein Ro is OH or is as defined below for $R_1$ below, to form $Y_2$-Pro-Arg-Ro, which is deprotected, if necessary under conversion to Pro-Arg-$R_1$, wherein $R_1$ is an enzymatically cleavable α-carboxy substituting group selected form esters, amides, anilides, hydrazides or L-amino acid esters, and thereafter reacting $Y_3$-C($Z_3$)-OH with Pro-Arg-$R_1$ to form $Y_3$-C($Z_3$)-Pro-Arg-$R_1$, which is deprotected to C-Pro-Arg-$R_1$, and then reacting $Y_4$-Ser-OH with C-Pro-Arg-$R_1$ to form $Y_4$-Ser-C-Pro-Arg-$R_1$, which is deprotected to Ser-C-Pro-Arg-$R_1$, and reacting $Y_5$-Asp($Z_5$)-OH with Ser-C-Pro-Arg-$R_1$ to form $Y_5$-Asp($Z_5$)-Ser-C-Pro-Arg-$R_1$, which is deprotected to the intermediate Asp-Ser-C-Pro-Arg-$R_1$, and finally removing the group $R_1$ with an enzyme, preferably trypsin to form Asp-Ser-C-Pro-Arg, or removing $R_1$ from $Y_5$-Asp($Z_5$)-Ser-C-Pro-Arg-$R_1$ before deprotection to Asp-Ser-C-Pro-Arg-OH.

The groups $Y_2$, $Y_3$, $Y_4$, $Y_5$, $Z_3$ and $Z_5$ are protective groups which apart from $Y_2$ are removable by catalytic hydrogenation. The employed synthesis strategy based on the combination hydrogenation/enzyme, both proceeding under mild conditions, leads to the peptides, in particular HEPP, in good yield without risk of formation of β-aspartyl peptides and cleavage of Asp-Pro bonds.

11 Claims, No Drawings

OTHER PUBLICATIONS

Proceedings of the 10th International Congress of Allergology, Jerusalem, Nov. 1979, Editors Oehling et al., Pergamon Press.

Hamburger, Immunology 38, p. 781 (1979).

Piszkiewicz et al., Biochem. Biophys. Res. Com. 40 p. 1173 (1970).

Merrifield, Recent Progress in Human Research 23, p. 459 (1967).

Schon et al., Int. J. Peptide Protein Res. 14, p. 485 (1979).

Wang et al., Int. J. Peptide Protein Res. 6, pp. 103–109 (1974).

Baba et al., Chem. Pharm. Bull. 21, pp. 207–209 (1973).

Bodanszky and Kwei, Int. J. Peptide Protein Res. 12, pp. 69–74 (1978).

Folsch, Acta Chem. Scand. 20, pp. 459–473 (1966).

Bodansky and Martinez, Synthesis, 5, pp. 333–356 (1981).

Bodanszky et al., J. Am. Chem. Soc. 89, 25, pp. 6753–6757 (1967).

Suzuki et al, Chemical & Pharm. Bull. 26(7) 2269–2274 (1978).

Suzulei et al, Chem. Pharm. Bull. 24(12) 3025–3033 (1976).

PROCESS FOR PRODUCING PENTAPEPTIDES AND INTERMEDIATES FOR USE IN THE SYNTHESIS

This is a continuation of application Ser. No. 07/493,508, filed Mar. 14, 1990, now abandoned.

The present invention relates to a special process for producing pentapeptides having the formula

H-Asp-Ser-C-Pro-Arg-OH wherein Asp, Ser, Pro and Arg may have L- or D-configuration and C denotes Asp or Asn in L- or D-configuration.

Thus the invention in particular relates to a process for producing the pentapeptide

Asp-Ser-Asp-Pro-Arg or the analogues thereof defined above.

Asp-Ser-Asp-Pro-Arg was first described by Hamburger, Science 189, p. 389, (1975), and is described in more detail in U.S. Pat. No. 4,171,299, which is incorporated herein by reference.

The peptide corresponds to the 320–324 amino acid sequence in the ε-chain in the $F_c$-region in human IgE, and has consequently been denoted HEPP (Human IgE pentapeptide), which denotation for reasons of simplicity is used in the following. More recent research has shown that the naturally occurring sequence presumably is Asp-Ser-Asn-Pro-Arg, and the synthesis of this peptide is thus also an important aspect of the present invention.

Hamburger demonstrated that HEPP was efficient in blocking allergic reactions in mammals, and later investigations have demonstrated its efficacy as anti-allergy agent. The compound is being clinically tested for treatment i.a. of allergic rhinitis and conjunctivitis.

According to U.S. Pat. No. 4,171,299 HEPP and the other IgE based peptides mentioned can purportedly be produced by classical peptide synthesis methods, such as solid-phase and solution-phase synthesis. The preferred synthesis is the so-called "Merrifield"-synthesis, cf. Merrified, J. Am. Chem. Soc. 85, p. 2149 (1963), where the individual amino acids are coupled stepwise to a growing peptide chain covalently bound to a solid resin particle, as further described and comprehensively exemplified in U.S. Pat. No. 4,171,299. Other synthesis methods have not been illustrated neither in the said patent specification nor in Hamburger's later articles.

In Proceedings of the 10th International Congress of Allergology, Jerusalem, November 1979, Editors Oehling et al., Pergamon Press, Hamburger reports a number of conflicting results form the investigations of the biological effects of HEPP performed by various groups of researchers. Hamburger offers the observed difficulties in synthesizing HEPP without entailing abnormal bonds and racemization, in particular in the Asp-Pro position as a possible explanation of these conflicting results.

Hamburger further emphasizes that Asp-Pro-bonds are particularly susceptible to decompose under acidic pH-conditions which often occur if lyophilizised HEPP is reconstituted in an inadequately buffered solution.

Hamburger launches similar considerations in Immunology 1979, 38, p. 781, where he had to defray from testing HEPP synthesized by two American laboratories.

Piszkiewicz et al., Biochem. Biophys. Res. Com. 40 p. 1173 (1970), demonstrated the acid lability of Asp-Pro bonds in a number of proteins in connection with sequence determination of proteins. Piszkiewicz explains that aspartyl-peptide bonds under acidic conditions generally undergo a reversible isomerization of the α-amide bond to a β-amide bond (α→β shift) via the cyclic α,β-imide intermediate, and further emphasizes Asp-Pro bonds as being particularly labile.

It should be noted that the isomerization tendency of the Asp-bond resulting in aspartimide formation constitutes a special problem associated with HEPP which also comprises an Asp-Ser bond. Aspartimide formation and the following α→β shift in peptides having Asp-Ser bonds have been demonstrated by Merrifield, Recent Progress in Human Research 23, p. 459, 1967.

The aspartimide formation has been comprehensively described in the literature. Thus, Schön et al., Int. J. Peptide Protein Res. 14, p. 485, 1979, declares with reference to numerous articles that imide formation is a wellknown side reaction in solution and solid-phase synthesis of aspartyl peptides and may occur both in acidic, basic and neutral media. Schön et al. describe various invain efforts to suppress the imide formation and report as their own observations that imide derivatives are even formed of aspartyl peptides having a free β-carboxyl group.

Wang et el., Int. J. Peptide Protein Res. 6, 1974, 103–109, describe conventional synthesis of a peptide having an Asp-Gly sequence ending with aspartimide compound as primary product. Product purification is impossible when there are both α- and β-compounds.

Baba et al., Chem. Pharm. Bull. 21, p. 207–209, 1973, demonstrated that the preferred deprotection agent hydrogen fluoride evoked aspartimide formation under acidic conditions in Asp(OBzl)-Ser(OBzl) bonds.

Several authors emphasize that Asp-Ser bonds are the ones most sensitive to aspartimide formation under basic conditions, among these authors Bodanszky and Kwei, Int. J. Peptide Protein Res. 12, p. 69–74, 1978; Fölsch, Acta Chem. Scand. 20, p. 459–473, 1966; Bodanszky and Martinez, Synthesis, 5, p. 333–356 (1981). Bodanszky et al., J. Am. Chem. Soc. 89, 25, p. 6753–57 (1967) describe a synthesis of secretin, a naturally occurring heptacosapeptide. A very small total yield is reported primarily due to aspartimide formation. Basic conditions were employed during the coupling procedures, acidic conditions during the deprotection stages and more or less neutral conditions during the purifications.

In the light of the above it is no wonder that the skilled person setting out to synthesize HEPP in reasonable yields and purity will encounter quite serious process technical problems, in particular due to the lability of the Asp-Ser and Asp-Pro bonds.

That this is also so in practice is illustrated by Suzuki et al., Chem. Pharm. Bull. 24, 12, p. 3025–3033 (1976). Here is first described the wellknown α→β shift in aspartyl peptides following the imide formation both in acidic and basic solution and even in hot alcohol. Further, reference is made to Baba et al., op.cit. who noted α→β shift in i.a. Asp-Ser sequences by deprotection with anhydrous HF, and a series of other works, and Suzuki arrives at the not surprising conclusion that suppression of the α→β side reaction is still an unsolved problem within the peptide chemistry. Suzuki consequently suggests a solution to the problem, in which HEPP is used as model peptide.

Starting from the HF-deprotection the suggested strategy consists in using protective groups which are stable against HF-treatment, such as β-phenacyl and β-p-nitrobenzylester and after the HF-treatment removing these β-carboxylic acid protective groups under mild conditions.

On this basis Suzuki et al. first carried out a solid-phase synthesis, in which a Boc-Asp(ONb)-Ser(Bzl)-Asp(ONb)-Pro-Arg(NO$_2$) resin was produced stepwise from Boc-Arg(NO$_2$)-OH, which was esterified to a chloromethylated styrene-copolymer resin, coupling with Boc-Asp-(ONb)-OH being performed in the last step. The resin was treated in traditional manner with a hydrogen fluoride anisole mixture, and the crude peptide obtained was hydrogenated for 7 hours to remove the (ONb) groups from Asp in the presence of Pd-on-carbon in water. Product was obtained in a yield of 22% calculated on Boc-Arg(NO$_2$) resin used. Suzuki has not described analysis of side products, but it is well known that hydrogenation of Arg(NO$_2$) gives rise to formation of ornithine, which it is difficult to remove.

In a parallel experiment Suzuki et al. used Boc-Asp(OBzl)-OH in the last coupling step, and the resin obtained is treated analogously with HF-anisole. A mixture of α- and β-aspartyl peptide was obtained, which was hard to separate.

Finally, Suzuki et al. performed a HEPP synthesis in solution-phase under mild conditions. It should be noted in particular that side-chain protected Ser (Boc-Ser(Bzl)-OH) was used, and that Boc-Asp(OBzl)-Ser(Bzl)-Asp(OBzl)-Pro-Arg(NO$_2$)-ONb was produced.

After removal of the BOC group with trifluoroacetic acid the resulting pentapeptide was dissolved in aqueous methanol and hydrogenated in the presence of Pd-on-carbon for 7 days. After 2 days of hydrogenation the Bzl-protective group on Ser had still not been removed, only traces of HEPP being detectable. After 7 days the yield was 25% corresponding to a total synthesis yield of only 8.2%.

In later experiments reported in Chem. Pharm. Bull 26(7)2269–2274(1978), and in an abbreviated version in Pept. Chem. 1977, 15th Edition, 33-6, Suzuki et al. used p-nitrobenzyl ester (ONb) as the side-chain protective group on Asp in order to minimize the α→β shift. Similarly, p-methoxybenzylsulfonyl (MBS) was used as the guanidino protective group on Arg.

Using the same synthesis strategy as in the earlier work Suzuki et al. produced the fully protected pentapeptide

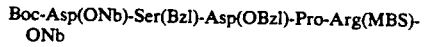
Boc-Asp(ONb)-Ser(Bzl)-Asp(OBzl)-Pro-Arg(MBS)-ONb

The protective groups except the two ONb-groups were removed by treatment with MsOH/anisole and in a subsequent step the ONb-groups were cleaved with zinc powder in 80% acetic acid or catalytic hydrogenation.

Although specific details are not given it seems that Suzuki's attempt to limit the α→β shift by using a different protective group gives rise to another shift, viz. an N to O acyl migration (N→O) shift.

On this background and in view of Hamburger's above works it can be established that until now no method of synthesizing HEPP has been described, which does not suffer from the disadvantages caused by the presence of Asp in the chain, and which makes possible uncomplicated synthesis of HEPP and the analogues in question in a satisfactory degree of purity and with commercially acceptable reaction times and reaction conditions, i.a. solid phase processes being unacceptably costly.

It is the object of the present invention to provide such a synthesis.

The invention rests on the surprising recognition that by varying some of the classical reaction conditions in solution-phase synthesis and terminating the synthesis by an enzymatic cleavage step it is possible to produce HEPP and the analogues in question in a very simple manner in good yield and without concurrent side reactions under formation of β-aspartyl peptides and cleavage of the Asp-Pro bond.

The key steps in the process according to the invention are as follows:

1. The starting compound used is Arg, which is not necessarily C-terminal protected or protected on the guanidino group.

2. The coupling of the Pro-unit is carried out in a medium comprising 20-70%, preferably 40-50% water.

3. An enzymatically cleavable C-terminal protective group capable of resisting catalytic hydrogenation is introduced on the Arg unit after the coupling with Pro, or Arg thus protected is used in the coupling.

4. Generally N-terminal and side-chain protective groups are used which are removable by catalytic hydrogenation under mild conditions.

5. The side-chain protective groups on Asp are removed under mild conditions immediately after the incorporation of the Asp-units simultaneously with the N-terminal protective group, and Asp and Asn are left side-chain unprotected in the further coupling of Ser.

6. Optional hydroxy protective groups on Ser are removed after the incorporation of the Ser unit before the final coupling to Asp.

7. The C-terminal protective group on Arg in the synthesized pentapeptide is removed enzymatically.

Thus, in accordance with the present invention the classical synthesis strategy is avoided in which use is normally made of the combinations base labile/acid labile; base labile/hydrogenation or acid labile/hydrogenation for removal or maintenance, respectively, of two different protective groups. In the synthesis according to the invention the combination hydrogenation/enzyme is used, both proceeding under mild conditions.

On this background the process according the invention is characterized by in an aqueous medium.

1) reacting optionally activated Y$_2$-Pro-OH, wherein Y$_2$ is an amino protective group, preferably belonging to the urethane class, with Arg-R$_o$, wherein R$_o$ is OH or as defined below for R$_1$, to form Y$_2$-Pro-Arg-R$_o$, which is deprotected, if necessary under conversion to a carboxy substituted derivative Pro-Arg-R$_1$, wherein R$_1$ is an enzymatically cleavable α- carboxyl substituting group capable of resisting catalytic hydrogenation, and being selected from esters —OR, where R denotes C$_1$-C$_7$ alkyl or optionally substituted aralkyl, preferably benzyl, amides or anilides —NR$_3$R$_4$, where R$_3$ and R$_4$ independently denotes H, C$_1$-C$_7$ alkyl, aralkyl or aryl, hydrazides —NHNHR$_5$, where R$_5$ is H, C$_1$-C$_5$ alkyl, aryl, CONH$_2$, or an amino acid residue in L-configuration or Gly or an amide or ester thereof, 2) reacting $Y_3$-C($Z_3$)-OH, wherein $Y_3$ is an amino protective group and $Z_3$ is a side-chain protective group, both being removable by hydrogenation, and where $Z_3$ is optional, when C is Asn, with Pro-Arg-$R_1$ in the presence of an activation agent to form $Y_3$-C($Z_3$)-Pro-Arg-$R_1$, which is deprotected, preferably by hydrogenation, to C-Pro-Arg-$R_1$, where C according to circumstances is Asp or Asn, 3) reacting optionally activated $Y_4$-Ser-OH, wherein $Y_4$ is a protective group being removable by hydrogenation, with C-Pro-Arg-$R_1$ to form $Y_4$-Ser-C-Pro-Arg-$R_1$, which is deprotected, preferably by hydrogenation, to Ser-C-Pro-Arg-$R_1$, and either 4) reacting optionally activated $Y_5$-Asp-($Z_5$)-OH, wherein $Y_5$ and $Z_5$ are protective groups being removable by hydrogenation, or $Y_5$ is an enzymatically cleavable protective group, with Ser-C-Pro-Arg-$R_1$ to form $Y_5$-Asp($Z_5$)-Ser-C-Pro-Arg-$R_1$, which is deprotected, preferably by hydrogenation, or according to circumstances enzymatically to Asp-Ser-C-Pro-Arg-$R_1$, and 5A) removing the group $R_1$ by treatment with an enzyme capable of cleaving α-carboxyl substituting groups from positively charged amino acids, to form Asp-Ser-C-Pro-Arg-OH, or 4B) reacting optionally activated $Y_5$-Asp($Z_5$)-OH, wherein $Y_5$ and $Z_5$ are protective groups being removable by hydrogenation, or $Y_5$ is an enzymatically cleavable protective group, with Ser-C-Pro-Arg-$R_1$ to form $Y_5$-Asp($Z_5$)-Ser-C-Pro-Arg-$R_1$, wherefrom the group $R_1$ is removed by treatment with an enzyme capable of cleaving α-carboxyl substituting groups from positively charged amino acids, to form $Y_5$-Asp-($Z_5$)-Ser-C-Pro-Arg-OH, and 5B) removing the groups $Y_5$ and $Z_5$, preferably by hydrogenation, or according to circumstances enzymatically to form Asp-Ser-C-Pro-Arg-OH.

If the process of the invention is compared with the above described prior art processes according to Hamburger and Suzuki, it will be apparent that they are fundamentally different.

According to the prior art processes the individual amino acids are always side-chain protected and before each coupling step only the amino terminal protective group is selectively removed generally under strongly acidic conditions. Thus the prior art processes lead to a fully protected pentapeptide, which is very difficult to deprotect without destroying the final product.

According to the process of the invention all protective groups except the C-terminal are removed simultaneously under mild conditions before the subsequent coupling. Thus the process leads to a pentapeptide which is only protected on the N-terminal Asp and on the C-terminal. This pentapeptide may easily be deprotected by catalytic hydrogenation and enzymatic cleavage, respectively.

It is a characteristic feature of the process according to the invention that use is made of an enzymatically cleavable α-carboxyl substituting group $R_1$, being capable of resisting catalytic hydrogenation.

According to the invention these can be selected from esters —OR, where R is $C_1$-$C_7$ alkyl, such as Me, Et, iPr, Pr, preferably Et, or optionally substituted aralkyl, preferably benzyl, amides or anilides —$NR_3R_4$, where $R_3$ and $R_4$ independently denotes H, which is preferred, but also $C_1$-$C_7$ alkyl, aralkyl, such as benzyl or aryl, hydrazides —$NHNHR_5$, where $R_5$ is H, $C_1$-$C_5$ alkyl, aralkyl, aryl or —$CONH_2$ (semicarbazide), or an amino acid in L-configuration or Gly or amides or esters thereof.

Use is made of free arginine, Arg-Ro, where Ro is OH, in the first coupling step with the Pro-unit, however, the α-carboxyl substituting group can also be present in the starting material (Ro=$R_1$).

As mentioned the amino protective groups $Y_3$, $Y_4$ and $Y_5$ used in the process according to the invention can be removed by catalytic hydrogenation, being the preferred deprotecting method. Generally the preferred hydrogenizable protective group is Z-, but also Fmoc and derivatives of both groups, may advantageously be used. The protective group $Y_2$ is not necessarily removable by catalytic hydrogenation. BOC, which is removable from the formed Boc-Pro-Arg-OH in hydrochloric ethanol with simultaneous esterification of Arg, is preferably used for introduction of the preferred C-terminal protective group -OEt.

Other suitable protective groups $Y_2$ preferably belong to the urethane class, e.g. Bpoc and 4-methoxybenzyloxycarbonyl and others have e.g. been mentioned in J. W. van Nispen in "Pure and Appl. Chem." vol. 59, 3, p. 331-344, 1987, and M. Bodanszky in "Principles of Peptide Synthesis" and "The Practice of Peptide Synthesis", both Springer-Verlag 1984, or in U.S. Pat. Nos. 4,339,534 and 4,420,424.

$Y_5$ may further be an enzymatically cleavable protective group, such as PGlu-, BzArg-, BzPro- and AcPhe-, cf. international application WO 89/06656.

In the individual coupling steps preferred use will be of the classical activation agents for formation of peptide bonds, such as DcC/HOBt/HONSu or isobutylchloroformiate. Other suitable agents are stated in U.S. Pat. No. 4,171,199, column 8.

Normally DCC/HOBt or DCC/HONSu are preferred, which give a more pure reaction and the smallest risk of racemization.

As regards optional side-chain protective groups these are also removable by catalytic hydrogenation.

For the side-chain protection of Asp use is preferably made of OBzl which is removable in one step together with the preferred N-terminal protective group Z-.

In traditional peptide synthesis use is normally made of tBU, which, however, is unsuited for use in the process according to the invention, because it cannot be removed under mild conditions, but demands an acidic environment.

The hydroxyl group in Ser is not necessarily protected, but can, if desired, be protected e.g. as aralkyl ether, in particular benzyl ether.

Suitable enzymes for cleaving $R_1$ are esterases, thiolendoproteases, serineendoproteases or carboxypeptidases, preferably selected from trypsin, bromelain, clostripain, endoproteinases ArgC, endoproteinase LysC, Achromobacter lyticus protease I, carboxypeptidase Y, carboxypeptidase MI or MII and carboxypeptidase P.

The preferred enzymne is trypsin, which is cheap and sufficiently reactive for the cleavage to be reasonably quick without risk of side reactions.

Dependent on the enzymes employed, cleaving can be carried out at pH 3.0-9.5; preferably, however, at pH 5.5-6.5, in particular 5.8-6.2, when the enzyme is trypsin.

If Y₅ is an enzymatically cleavable group it can be cleaved off in the same or a separate enzymatic treatment step dependent on the nature of the group and the necessary enzyme specificity derived therefrom, which is well known to a person skilled in enzymology.

The following can be said about the individual reaction steps:

Step 1 normally comprises a classical activation of the Pro-reactant, preferably being BOC-Pro-OH with isobutylchloroformate in tetrahydrofuran, acetone or another organic water miscible solvent, and HONSu is added to form the active ester Boc-Pro-OnSu.

Free arginine is dissolved in water, and pH is adjusted to 7.0–12.0, preferably 8.5–9.0. The solution is mixed with the Boc-Pro-ONSu solution, and the product Boc-Pro-Arg-OH is formed.

The product is further converted to Pro-Arg-R₁, preferably Pro-Arg-OEt, as the C-terminal must be blocked, partly for reasons of solubility, and partly for reasons of synthesis in the further course.

Alternatively, Arg-R₁ can be used as starting material.

Step 2 is carried out in classical manner by solution-phase synthesis, the last stage being a catalytic hydrogenation, preferably with Pd-on-carbon.

In Step 3 the β-side-chain protective group on Asp or Asn is normally omitted, likewise in steps 4 and 5.

The preferred Asp-reactant in both steps 2 and 4 is Z-Asp(OBzl)-OH, the Z- and the OBzl-groups both being removable simultaneously under mild conditions, i.e. catalytic hydrogenation in a mildly acidic to neutral environment. This entails that the base and acid labile Asp-Ser bond does not undergo α→β shift, and that the acid labile Asp-Pro bond is not hydrolyzed.

The invention also relates to a number of novel intermediates.

A first type of intermediates are the protected pentapeptide derivatives of the formula

Y₅-Asp(Z₅)-Ser-Asp-Pro-Arg-R₀ where Y₅ and Z₅ are protective groups being removable by hydrogenation, while R₀ is OH or is an enzymatically cleavable protective group R₁, as earlier defined, which can resist catalytic hydrogenation.

This type of derivatives does not encompass Suzuki's partially deprotected compounds since of course ONb is not resistant to hydrogenation.

The preferred intermediates are

Z-Asp(OBzl)-Ser-Asp-Pro-Arg-OEt and the C-terminal deprotected

Z-Asp(OBzl)-Ser-Asp-Pro-Arg-OH both being easily deprotectable as earlier described.

Another group of intermediates are

Asp-Ser-Asp-Pro-Arg-R₁, where R₁ is as earlier defined, apart form methyl, R₁ preferably being ethyl.

The methyl ester is described by Hamburger (U.S. Pat. No. 4,177,299), who also mentions the corresponding ethyl, propyl, butyl, hexyl, octyl, decyl and dodecyl esters. However, Hamburger does not give any physical data or other evidence that these esters have actually been made.

In the following the process according to the invention is described in more detail by way of examples.

The present description employs the usual abbreviations within peptide chemistry. The amino acid symbols are in accordance with IUPAC-IUB Commission on Biochemical Nomenclature, and the amino acids are in L-form unless otherwise stipulated. The following additional abbreviations are used:

Z=Cbz=benzyloxycarbonyl
Boc=tert. butoxycarbonyl
Me=methyl
Et=ethyl
tBu=tert. butyl
Ac=acetyl
Bzl=benzyl
Bz=benzoyl
iPr=isopropyl
Pr=propyl
HONSu=N-hydroxysuccinimide
DCC=dicyclohexylcarbodiimide
DMF=dimethylformamide
NMM=N-methylmorpholine
TEA=triethylamine
HOBT=1-hydroxybenzo-triazol
Fmoc=9-fluoroenyl-methyloxycarbonyl
ONb=p-nitrobenzylester
Bpoc=biphenyloxycarbonyl
DCU=dicyclohexylurea

EXAMPLE

Synthesis of H-Asp-Ser-Asp-Pro-Arg-OH

1. Synthesis of H-Pro-Arg-OEt, 2×HCl

Reaction Scheme

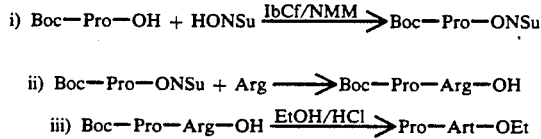

i) Boc—Pro—OH + HONSu $\xrightarrow{\text{IbCf/NMM}}$ Boc—Pro—ONSu ii) Boc—Pro—ONSu + Arg $\longrightarrow$ Boc—Pro—Arg—OH iii) Boc—Pro—Arg—OH $\xrightarrow{\text{EtOH/HCl}}$ Pro—Arr—OEt 100 g Boc-Pro-OH (464.7 mmole) are dissolved in 1:1 acetone and admixed with 52.5 g N-methylmorpholine (518.8 mmole). The solution is cooled to −8° C., and 60.0 g isobutylchloroformiate (440.0 mmole) are added, succeeded by 55.9 g N-hydroxysuccineimide (485.7 mmole) and 52.5 g N-methylmorpholine (518.8 mmole). To this solution is added a solution of 84.8 g arginine (486.8 mmole) cooled to 2° C. dissolved in 400 ml water and 300 g ice. pH is adjusted to 8.5 and kept at this value until reaction is complete, whereafter the product is precipitated and dried.

The dried Boc-Pro-Arg-OE is dissolved in 900 ml ethanol, being 1.5N as regards HCl. After removal of the Boc-group and esterification of Pro-Arg-OH the hydrochloric ethanol is evaporated in vacuo.

Yield: 141.9 g, 82%.
Amino acid analysis: Pro: 0.95, Arg: 1.05.
Purity by HPLC: 96%.

2. Synthesis of H-Asp-Pro-Arg-OEt, CH₃COOH

Reaction scheme:

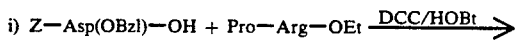

i) Z—Asp(OBzl)—OH + Pro—Arg—OEt $\xrightarrow{\text{DCC/HOBt}}$

-continued

Reaction scheme:

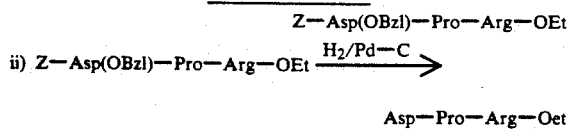

Procedure 62.5 g Z-Asp(OBzl)-OH (74.9 mmole), 7.0 g HOBt (51.8 mmole), 65.0 g Pro-Arg-OEt, 2HCl and 20 g NMM (197.6 mmole) are dissolved in 500 ml DMF, and the mixture is cooled to 0° C., whereafter 40.0 g DCC (193.9 mmole) are added. Upon complete reaction DCU is filtered off, and the product is purified by means of ion exchange chromatography and RP-HPLC C-18 columns. The pure product fractions are concentrated to a suitable volume and admixed with 6 g 5% Pd-on-carbon, hydrogenation being on a Parr-hydrogenation apparatus at a hydrogen pressure of 2 bar. Upon complete reaction filtration is performed, and the reaction mixture is evaporated to dryness.

Yield: 69.7 g, 84%.
Acetate content: 16.3%.
Amino acid Analysis: Asp: 0.92, Arg: 1.00, Pro: 1.00.
Purity by HPLC: 91%

3. Synthesis of Ser-Asp-Pro-Arg-OEt, 2xCH$_3$COOH

Reaction scheme:

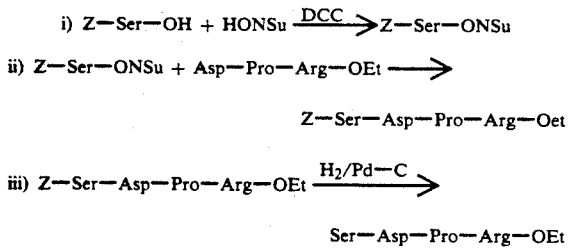

Procedure 29.5 g Z-Ser-OH (123.3 mmole) and 16.2 g HONSu (140.7 mmole) are dissolved in 143 ml DMF and cooled to 0° C. Hereafter a cooled solution of 24.0 g DCC (116.3 mmole) dissolved in 35 ml DMF is added. Upon formation of Z-Ser-ONSu the solution is filtered and poured into a 0° C. solution comprising 50 g Asp-Pro-Arg-OEt, CH$_3$COOH (105.4 mmole) and 6 ml NMM (54 mmole) dissolved in 140 ml DMF.

The reaction mixture is diluted with water, and purification is made on ion exchange material succeeded by purification on RP-HPLC C-18 material. The pure product fractions are concentrated to a suitable volume and admixed with 5 g 5% Pd-on-carbon, hydrogenation being on a Parr-hydrogenation apparatus at a hydrogen pressure of 2 bar. Upon complete reaction the solution is filtered and evaporated to dryness.

Yield: 52 g, 80%.
Water content: 2.5%.
Acetate content: 7.4%.
Amino acid analysis: Asp: 1.03, Ser: 0.95, Arg: 0.96, Pro: 1.07.
Purity by HPLC: 96.9%.

4. Synthesis of Asp-Ser-Asp-Pro-Arg-OEt

Reaction scheme:

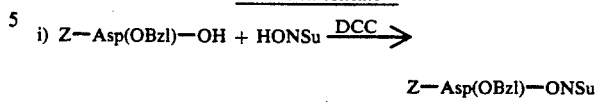

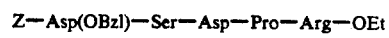

Procedure 39.2 g Z-Asp(OBzl)-OH (109 mmole) and 12.7 g HONSu (110.0 mmole) are dissolved in 150 ml DMF and cooled to 0° C. A 0° C. solution of 226 g DCC (109.8 mmole) in 25 ml DMF is added. Upon complete reaction filtration is performed for DCU, and the solution is mixed with a 0° C. solution comprising 62.0 g Ser-Asp-Pro-Arg-OEt, 2AcOH (100.0 mmole) and 12.0 ml NMM (108.0 mmole) dissolved in 125 ml DMF. Upon complete reaction the product is purified on RP-HPLC C-18 material. The pure product fractions are concentrated to a suitable volume and 5 g 5% Pd-on-carbon is added and hydrogenated on a Parr-hydrogenation apparatus at a hydrogen pressure of 2 bar. Upon complete reaction the solution is filtered and the product is brought on dry form by freeze-drying.

Yield: 51.8 g, 84%.
Acetate content: 9.0%.
Water content: 2.1%.
Amino acid analysis: Asp: 1.94, Ser: 0.87, Arg: 1.08, Pro: 0.99.
Purity by HPLC: 97.1%.

5. Synthesis of H-Asp-Ser-Asp-Pro-Arg-OH

Reaction scheme:

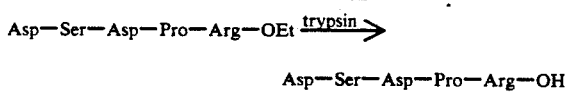

Procedure 25 g Asp-Ser-Asp-Pro-Arg-OEt (40.5 mmole) are dissolved in 200 ml water and pH is adjusted to 6.0, whereafter 30 mg trypsin (1.27 μmmole) in 1 ml water are added. For the duration of the reaction pH is kept constant at 6.0. Upon complete reaction the product is purified on ion exchange material and RP-HPLC C-18 material. The pure product fractions are concentrated and freeze-dried.

Yield: 19.1 g, 80.1%.
Residue on ignition: 0.01%.
Optical rotation: −92.9°.
Acetate content: 1.0%.
Water content: 3.0%.
Amino acid analysis: Asp: 1.96, Ser: 0.89, Arg: 1.07, Pro: 0.98.
Purity by HPLC: 98.5%.

What is claimed is:

1. A process for producing pentapeptides having the formula

H-Asp-Ser-X-Pro-Arg-OH wherein X is Asp or Asn in L- or D-configuration, and each of Asp, Ser, Pro and Arg may independently have L- or D-configuration,
said process comprising:
1) a. reacting $Y_2$-Pro-OH with Arg-$R_o$ to form $Y_2$-Pro-Arg-$R_o$, wherein $Y_2$ is an amino protective group, and $R_o$ is —OH or is as defined below for $R_1$,
b. the resulting $Y_2$-Pro-Arg-$R_o$ then being deprotected to form Pro-Arg-$R_o$, and, when $R_o$ is —OH, also converted to a carboxyl substituted derivative, Pro-Arg-$R_1$, wherein $R_1$, is an enzymatically cleavable α-carboxyl substituting group capable of resisting catalytic hydrogenation, $R_1$ being selected from the group consisting of: i) esters —OR, where R denotes $C_1$-$C_7$ alkyl, aralkyl or substituted aralkyl: ii) amides or anilides —$NR_3R_4$, where $R_3$ and $R_4$ independently denote H, $C_1$-$C_5$ alkyl, aryl, $CONH_2$; and iii) amino acid residues in L-configuration, Gly and their amides and esters,
2) a. reacting $Y_3$-X($Z_3$)-OH with Pro-Arg-$R_1$ in the presence of an activation agent so as to form $Y_3$-X($Z_3$)-Pro-Arg-$R_1$, wherein: $Y_3$ is an amino protective group removable by hydrogenation; and, when X is Asp, $Z_3$ is a side-chain protective group removable by hydrogenation, and, when X is Asn, $Z_3$ is either a side-chain protective group removable by hydrogenation or $Z_3$ is hydrogen,
b. the resulting $Y_3$-X($Z_3$)-Pro-Arg-$R_1$ then being deprotected so as to form X-Pro-Arg-$R_1$,
3) reacting $Y_4$-Ser-OH with X-Pro-Arg-$R_1$ to form $Y_4$-Ser-X-Pro-Arg-$R_1$, wherein $Y_4$ is a protective group being removable by hydrogenation, $Y_4$-Ser-X-Pro-Arg-$R_1$ being deprotected so as to form Ser-X-Pro-Arg-$R_1$, and
either,
4A) reacting $Y_5$-Asp-($Z_5$)-OH with Ser-X-Pro-Arg-$R_1$ so as to form $Y_5$Asp($Z_5$)-Ser-X-Pro-Arg-$R_1$, wherein $Y_5$ is a protective group removable by hydrogenation or an enzymatically cleavable protective group, and $Z_5$ is a protective group removable by hydrogenation, the resulting $Y_5$-Asp($Z_5$)-Ser-X-Pro-Arg-$R_1$ then being deprotected so as to form Asp-Ser-X-Pro-Arg-$R_1$, and then,
5A) removing the group $R_1$ by treatment with an enzyme capable of cleaving α-carboxyl substituting groups from positively charged amino acids, to form the desired Asp-Ser-X-Pro-Arg-OH,
or
4B) reacting $Y_5$-Asp($Z_5$)-OH with Ser-X-Arg-$R_1$ to form $Y_5$-Asp($Z_5$)-Ser-X-Pro-Arg-$R_1$, wherein $Y_5$ is a protective group being removable by hydrogenation or an enzymatically cleavable protective group, and $Z_5$ is a protective group removable by hydrogenation, the group $R_1$ being removed from the resulting $Y_5$-Asp($Z_5$)-Ser-X-Pro-Arg-$R_1$ by treatment with an enzyme capable of cleaving α-carboxyl substituting groups from positively charged amino acids, to form $Y_5$-Asp-($Z_5$)-Ser-X-Pro-Arg-OH, and then
5B) removing the groups $Y_5$ and $Z_5$ so as to form the desired Asp-Ser-X-Pro-Arg-OH,
said process being further characterized in that the protective groups $Y_3$, $Z_3$, $Y_4$, and $Z_5$ are removed by hydrogenation.

2. A process according to claim 1, wherein one or more of the said $Y_2$-Pro-OH, $Y_3$-X($Z_3$)-OH, $Y_4$-Ser-OH and $Y_5$-Asp($Z_5$)-OH are activated before said reactions.

3. A process according to claim 1, wherein the protective group $Y_5$ is removed by hydrogenation.

4. A process according to claim 1, wherein the protective groups $Y_5$ and $R_1$ are removed enzymatically.

5. A process according to claim 1, wherein in step 1), Boc-Pro-ONSu is reacted with free Arg-OH at pH 7.0–12.0 in 20–70% aqueous medium and the resulting Boc-Pro-Arg-OH is converted to Pro-Arg-$OR_2$, where $R_2$ is $C_1$-$C_7$ alkyl, benzyl or substituted benzyl, by treatment with acidic R-OH.

6. A process according to claim 1, wherein in step 2) Z-Asp(OBzl)-OH is reacted with Pro-Arg-OR to form Z-Asp(OBzl)-Pro-Arg-OR and the Z- OBzl-protective groups are simultaneously removed by catalytical hydrogenation.

7. A process according to claim 1, wherein in step 3) Z-Ser-ONSu is reacted with Asp-Pro-Arg-OR and Z is removed, by catalytic hydrogenation.

8. A process according to claim 1, wherein in step 4A) or 5B) Z-Asp(ABzl)-ONSu is reacted with Ser-Asp-Pro-Arg-OR in basic medium to form Z-Asp(OBzl)-Ser-Asp-Pro-Arg-OR and the protective groups Z- and OBzl are removed simultaneously by catalytic hydrogenation.

9. A process according to claim 1, wherein in step 5A) or 4B) the group $R_1$ or R is removed by treatment with an esterase, a thiolendoprotease, a serine endoprotease or a carboxypeptidase.

10. A process according to claim 9, wherein the group $R_1$ or R is removed by treatment with an enzyme selected from the group consisting of trypsin, bromelain, clostripain, endoproteinase ArgC, endoproteinase LysC, Achromobacter lyticus protease I, carboxypeptidase Y, carboxypeptidase MI and MII and carboxypeptidase P.

11. A process according to claim 10, wherein the group $R_1$ or R is removed by treatment with trypsin at pH 3.0–9.5.

* * * * *